US010641726B2

(12) United States Patent
Kuo et al.

(10) Patent No.: US 10,641,726 B2
(45) Date of Patent: May 5, 2020

(54) FABRICATION OF A NANOCHANNEL FOR DNA SEQUENCING USING ELECTRICAL PLATING TO ACHIEVE TUNNELING ELECTRODE GAP

(71) Applicant: SEAGATE TECHNOLOGY LLC, Cupertino, CA (US)

(72) Inventors: David S. Kuo, Palo Alto, CA (US); Xiaomin Yang, Livermore, CA (US); ShuaiGang Xiao, Fremont, CA (US); Kim Yang Lee, Fremont, CA (US); Koichi Wago, Sunnyvale, CA (US); Thomas Young Chang, Menlo Park, CA (US)

(73) Assignee: SEAGATE TECHNOLOGY LLC, Cupertino, CA (US)

( * ) Notice: Subject to any disclaimer, the term of this patent is extended or adjusted under 35 U.S.C. 154(b) by 107 days.

(21) Appl. No.: 15/886,581

(22) Filed: Feb. 1, 2018

(65) Prior Publication Data

US 2018/0217083 A1     Aug. 2, 2018

Related U.S. Application Data

(60) Provisional application No. 62/453,339, filed on Feb. 1, 2017.

(51) Int. Cl.
| | | |
|---|---|---|
| *G01N 27/327* | (2006.01) | |
| *B01L 3/00* | (2006.01) | |
| *B81C 1/00* | (2006.01) | |
| *G01N 33/487* | (2006.01) | |
| *C12Q 1/6869* | (2018.01) | |
| *C12Q 1/6809* | (2018.01) | |
| *B82Y 5/00* | (2011.01) | |

(52) U.S. Cl.
CPC .... *G01N 27/3278* (2013.01); *B01L 3/502707* (2013.01); *B01L 3/502715* (2013.01); *B81C 1/00547* (2013.01); *C12Q 1/6869* (2013.01); *G01N 33/48721* (2013.01); *B82Y 5/00* (2013.01); *C12Q 1/6809* (2013.01)

(58) Field of Classification Search
CPC .............................................. G01N 33/48721
See application file for complete search history.

(56) References Cited

U.S. PATENT DOCUMENTS

| | | |
|---|---|---|
| 5,007,984 A | 4/1991 | Tsutsumi et al. |
| 5,071,714 A | 12/1991 | Rodbell et al. |
| (Continued) | | |

FOREIGN PATENT DOCUMENTS

WO      2015-057870 A1      4/2015

OTHER PUBLICATIONS

Duan et al., "Review article: Fabrication of nanofluidic devices," Biomicrofluidics 7, 026501 (2013).

(Continued)

*Primary Examiner* — Alexander S Noguerola
(74) *Attorney, Agent, or Firm* — Holzer Patel Drennan

(57) ABSTRACT

A DNA sequencing device, and related methods, include a nanopore or nanochannel structure, and a nanoelectrode. The nanoelectrode includes electrode members having free ends exposed within the nanopore or nanochannel structure, an electrode gap defined between of the free ends, and plated portions formed on the free ends to provide a reduced sized for the electrode gap.

11 Claims, 11 Drawing Sheets

(56) References Cited

U.S. PATENT DOCUMENTS

| | | | |
|---|---|---|---|
| 5,127,989 | A | 7/1992 | Haraguchi et al. |
| 6,627,067 | B1 | 9/2003 | Branton et al. |
| 7,582,490 | B2 | 9/2009 | Golovchenko et al. |
| 8,105,471 | B1 | 1/2012 | Han et al. |
| 9,410,923 | B2 | 8/2016 | Sauer et al. |
| 10,247,700 | B2 | 4/2019 | Hu et al. |
| 10,413,903 | B2 | 9/2019 | Taniguichi |
| 2002/0039737 | A1 | 4/2002 | Chan et al. |
| 2010/0188109 | A1* | 7/2010 | Edel .................. B82Y 15/00 324/693 |
| 2010/0267158 | A1 | 10/2010 | Chou et al. |
| 2011/0174629 | A1* | 7/2011 | Bouchet ............ B81C 1/00206 205/131 |
| 2013/0334047 | A1 | 12/2013 | Jeong et al. |
| 2014/0151228 | A1 | 6/2014 | Royyuru et al. |
| 2014/0312002 | A1* | 10/2014 | Peng .................... C12Q 1/6869 216/17 |
| 2016/0153105 | A1* | 6/2016 | Gumbercht ......... B81C 1/00087 205/112 |
| 2016/0319342 | A1 | 11/2016 | Kawai |
| 2017/0144158 | A1 | 5/2017 | Taniguchi |
| 2017/0146510 | A1 | 5/2017 | Ikeda et al. |
| 2017/0253479 | A1 | 9/2017 | Nikoobakht, IV |
| 2018/0120287 | A1* | 5/2018 | Henck ................. C12Q 1/6869 |

OTHER PUBLICATIONS

Di Ventra, Massimiliano, et al., "Decoding DNA, RNA and peptides with quantum tunneling," Nature Nanotechnology, vol. 11, Feb. 2016, pp. 117-126.

Feng, Yanxiao, et al., "Nanopore-based Fourth-generation DNA Sequencing Technology," Genomics Proteomics Bioinformatics, 13 (2015), pp. 4-16.

Ivanov, A.P., et al., "DNA Tunneling Detector Embedded in a Nanopore," Nano Letters, 2011, 11, pp. 279-285.

Ke, Rongqin, et al., "Fourth Generation of Next-Generation Sequencing Technologies: Promise and Consequences," Human Mutation, vol. 37, No. 12, 2016, pp. 1363-1367.

Kulski, Jerzy K., "Next-Generation Sequencing—An Overview of the History, Tools, and 'Omic' Applications," http://dx.doi.org/10.5772/61964, 59 pages.

* cited by examiner

FABRICATION OF A NANOCHANNEL FOR DNA SEQUENCING USING ELECTRICAL PLATING TO ACHIEVE TUNNELING ELECTRODE GAP

RELATED APPLICATIONS

This application claims the benefit of the filing date of U.S. Provisional Application No. 62/453,339, filed on 1 Feb. 2017, and entitled FABRICATION OF A NANO-CHANNEL FOR DNA SEQUENCING USING ELECTRICAL PLATING TO ACHIEVE TUNNELING ELECTRODE GAP, the disclosure of which is incorporated in its entirety by this reference.

SUMMARY

The present disclosure relates to fabricating a narrow channel for a nanoelectrode for use in deoxyribonucleic acid (DNA) sequencing. The methods and devices disclosed herein provide formation of a tunneling electrode (e.g., an electrode having electrode members that are spaced apart by an initial gap size of about 10 nm or greater), followed by electrode plating or other additive process to add material to the exposed portions of the electrodes to reduce the gap until reaching a dimensional range on the order of about 1 nm (e.g., about 0.3 nm to about 2.0 nm, and more particularly in the range of about 0.1 nm to about 1.0 nm).

Another aspect of the present disclosure relates to a method of fabricating a nanoelectrode DNA sequencing device. The method includes forming a nanopore or nanochannel structure, forming a nanoelectrode having an electrode gap exposed within the nanopore or nanochannel, and plating at least portions of the nanoelectrode with a plating material to reduce a size of the electrode gap.

The reduced size of the electrode gap may be in the range of about 0.3 nm to about 2 nm. The nanochannel and the plating material may include a metallic material. The portions of the nanoelectrode that are plated may include end surfaces of the nanoelectrode that are exposed within the nanopore or nanochannel. The portions of the nanoelectrode that are plated may include top surfaces of the nanoelectrode arranged perpendicular to the end surfaces. The method may further include lithography patterning the nanochannel in a resistor layer and an insulator substrate, and forming a nanoelectrode includes forming a tunneling electrode in the nanochannel. The method may include forming a pair of contact pad openings for DNA channeling by lithography and etching into the insulator substrate, filling the contact pad openings with contact pad material to form contact pads, forming the nanopore or nanochannel structure includes lithography patterning a DNA channel between the contact pads, depositing an insulator material over the contact pads and DNA channel, forming the nanopore or nanochannel structure with the electrode gap exposed within the nanopore or nanochannel, and depositing a sealing layer over the nanopore or nanochannel. The etching into the insulator substrate may include reactive ion etching (RIE). The lithography patterning may include at least one of deep ultraviolet (DUV) lithography, 193 nm lithography, e-beam lithography, and nano-imprint lithography (NIL). Forming the tunneling electrode in the nanochannel may include a Chromium (Cr) liftoff process followed by stripping a resistive layer.

Another aspect of the present disclosure relates to a DNA sequencing device that includes a nanopore or nanochannel structure, and a nanoelectrode. The nanoelectrode includes electrode members having free ends exposed within the nanopore or nanochannel structure, an electrode gap defined between of the free ends, and plated portions formed on the free ends to provide a reduced sized for the electrode gap.

The nanopore or nanochannel structure may be formed in an insulator substrate, and the insulator substrate may include SiO2 or glass. The nanopore or nanochannel structure may have a width in the range of about 10 nm to about 20 nm. The electrode gap may have a width in a range of about 0.3 nm to about 2.0 nm. The device may further include electrode contacts electrically connected to the nanoelectrode, and a controller electrically connected to the electrode contacts and operable to detect an electronic signal measured between the electrode members. The device may further include an energy source operable to draw a DNA strand through the nanopore or nanochannel.

Another aspect of the present disclosure relates to a method of DNA sequencing. The method may include providing a DNA sequencing device having a nanopore or nanochannel structure, and a nanoelectrode, the nanoelectrode having first and second electrode members with free ends exposed within the nanopore or nanochannel structure, an electrode gap defined between of the free ends, and plated portions formed on the free ends to provide a reduced size for the electrode gap. The method may further include drawing a DNA strand through the nanopore or nanochannel and the electrode gap, detecting, with the nanoelectrode, electronic signals associated with separate nucleotides of the DNA strand, and determining an order of the nucleotides based on the detected electronic signals.

The method may include further reducing the size of the electrode gap with additional plating. The plated portions may include a different material from the first and second electrode members. The DNA sequencing device may further include a controller operable to conduct the determining of the order of the nucleotides.

In one embodiment, a method of fabricating a nanochannel for DNA sequencing includes lithography patterning a tunneling electrode trench or channel in a resistor layer and an insulator substrate, forming a tunneling electrode in the channel, stripping the resistor layer from the tunneling electrode, forming a pair of contact pad openings for DNA channeling by lithography and etching into the substrate, filling the contact pad openings with contact pad material, lithography patterning a DNA channel between the contact pads, depositing an insulator material over the contact pads and DNA channel, forming a tunneling electrode gap in the DNA channel, and depositing a sealing layer.

The insulator substrate may include SiO2 or glass. The tunneling electrode channel may have a width in the range of about 10 nm to about 20 nm. The tunneling electrode channel may have a height in the range of about 10 nm to about 20 nm. Conducting the lithography patterning of the channel may include using at least one of deep ultraviolet (DUV) lithography, 193 nm lithography, e-beam lithography, and nano-imprint lithography (NIL). The method may include etching in the insulator substrate using reactive ion etching (RIE). Forming the tunneling electrode in the channel may include Chromium (Cr) liftoff process followed by stripping a resistive layer. The DNA channel may have a width in the range of about 5 nm to about 10 nm, and a height in the range of about 10 nm to about 20 nm. The insulator layer may comprise SiO2. The gap may have a width in a range of about 0.1 n. to about 1.0 nm. Forming the tunneling electrode gap may include electrode plating. Depositing the sealing layer may include depositing Polydimethylsiloxane (pdms).

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components—including those having a dash and a second reference label—apply to other similar components. If only the first reference label is used in the specification, the description is applicable to any one of the similar components having the same first reference label irrespective of the second reference label.

DETAILED DESCRIPTION

Figure 1A:
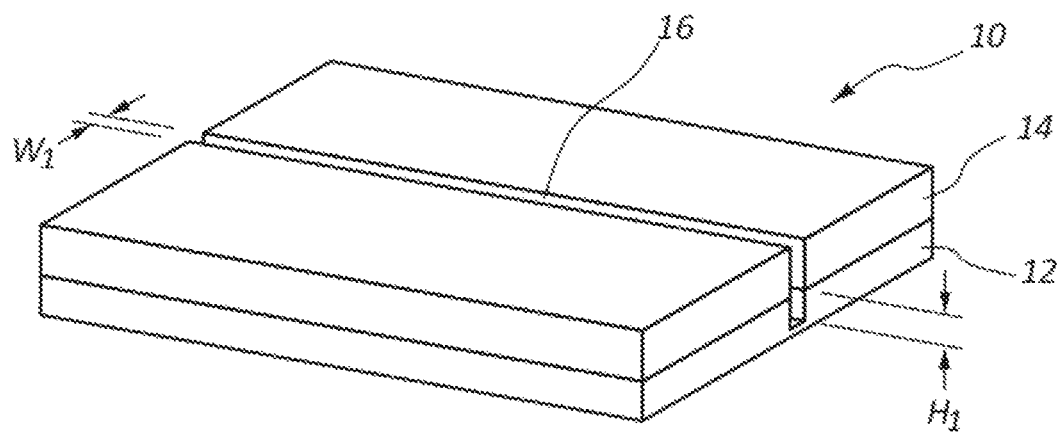
FIGS. 1A-1H show process steps for forming a DNA nanofluidic channel in accordance with the present disclosure.

Despite considerable efforts, DNA sequencing today still suffers from high costs and low speeds. To address all these issues, various methods have been proposed over the past decade that would allow individual DNA strands to be read directly. Among these, nanopore and nanochannel based approaches have emerged as the most promising. However, many challenges exist related to fabricating a channel and/or pore opening that is sufficiently small to limit passage to a single DNA strand, and there is no such report of a relatively mature method that address this unmet need.

Direct DNA sequencing has drawn attention due to its advantages on long read length, high throughput and low cost. Direct DNA sequencing methods using transverse tunneling current measurement have been studied extensively in literature. However, a manufacturably viable direct DNA sequencing device with required dimensions for the gap between the nanoelectrodes, nor methods for creating such a device, have not been discovered. Conventional MEMS and nanofabrication methods are inadequate for creating the required structure.

Direct measure of individual nucleotides of long DNA strands rapidly and with low cost is one goal of DNA sequencing. Among these options, nanopore- and nanochannel-based approaches that measure a transverse signal across individual nucleotides have emerged as a promising approach. The general approach involves electrically driving DNA and RNA strands through a nanopore or narrow channel via ionic flow or driven by a pressure gradient. As the strand passes a high resolution sensor embedded inside the channel, the high spatial resolution sensor measures the unique properties of the individual nucleotides (A,T,C,G). One type of sensor would consist of a conductive electrode that measures the unique tunneling currents associated with the nucleotide, thereby identifying and resolving the four unique nucleotide types.

However, there are several significant challenges associated with the fabrication of such devices at relatively low cost that can spatially resolve individual nucleotides of each strand, wherein nucleotides are on the order of about 1 nm is size in a transverse direction. One challenge is the ability to fabricate a channel width on the order of about 1 nm (e.g., in the range of about 0.3 nm to about 2 nm) with accuracy and repeatability to obtain tunneling current that is exponential verses distance. Such a channel or pore is sometimes referred to as a nanochannel or nanopore. For example, the signal tunneling current would reduce by a factor of about 1000× if spacing is increased between electrode and base molecule by only about 0.5 nm. A second challenge relates to fabrication of a sensor or nanoelectrode that is on the order of about 1 nm in spacing between the electrodes in order to resolve and detect individual nucleotides (e.g., A,T,C,G) in the DNA strand.

The present disclosure generally relates to DNA sequencing, and more particularly relates to DNA sequencing devices having nanochannels and nanoelectrodes, and related methods of fabricating such devices. The present disclosure may also relate to DNA sequencing using such devices.

The present disclosure also relates to methods and associated devices and systems for fabricating a DNA nanochannel with a very small tunneling electrode width (e.g., less than about 1 nm), as well as the resultant DNA nanochannel itself. The disclosed methods may include fabricating a narrow tunneling electrode first (e.g., having a width of about 10 nm between spaced apart electrode members), and then using electrode plating to close the gap between the electrode members until reaching a dimensional range of about 0.3 nm and about 2 nm, and more particularly about 0.1 nm to about 1 nm. The resultant tunneling electrode may be used to measure a DNA strand passing through the nanochannel.

A relatively fast and low-cost genome (DNA), transcriptome (RNA) and proteome (all proteins) sequencing method could lead to the development of personalized medicine (e.g., the ability to target drugs and medical treatments specially to an individual). However, to fabricate a nanochannel for single molecular DNA sequencing is still technically challenging due to the extremely small dimensions involved with the devices used to conduct the sequencing. The devices and methods disclosed herein address at least some of these challenges.

To improve DNA sequencing throughput and lower the cost, direct-reading sequencing device like nanochannel devices based on, for example, (1) semiconductor nanochannel, and (2) transverse electron current measurement may be highly desirable.

A nanochannel structure with a pair of transverse electrodes can be fabricated using conventional nanofabrication processes. A limitation of this structure is the relatively wide nanogap between two electrodes defined by lithography, which is typically in the range of 10 nm to about 30 nm. Ideally a small nanogap between two electrodes on the order of about 0.3 nm and about 2 nm (more particularly on the order of about 1 nm) is preferred to enhance the signal-to-noise ratio during transverse current detection due to the ultrasmall diameter of DNA single strand (~1 nm). The present disclosure relates to a new design for a nanochannel with two transverse electrodes having a uniform, ultrasmall nanogap on the order of about 1 nm (e.g., in the range of about 0.3 nm to about 2 nm). A fabrication process flow to create this nanogap structure is described as well.

FIGS. 1A-1H illustrate example fabrication steps for formation of a DNA sequencing device 10. While particular fabrication steps, materials, structures and features are shown with references to FIGS. 1A-1H, other options are available for fabricating the DNA sequencing device 10. One aspect of DNA sequencing device 10 unique to many of the embodiments disclosed herein is use of plating techniques and/or plated features associated with one or more electrodes of the DNA sequencing device. The plated features may be used to adjust a gap size between electrode members of a nanoelectrode associated with a nanochannel or nanopore of the DNA sequencing device. A gap or spacing between the electrode members exposed within the nanochannel and/or nanopore may initially have a spacing that is substantially equal to a width of the nanochannel or nanopore. The gap between the electrode members within the nanochannel may be reduced using plating processes and/or techniques to within a desired range (e.g., on the order of about 1 nm, and particularly to about 0.3 nm to about 2 nm). The plated tips may also provide a reduced cross-sectional area for the surfaces of the electrode members facing each other as part of the defined gap. This reduced surface area may help reduce the noise in the electronic signal collected by the DNA sequencing device as a DNA strand passes through the electrode gap, thereby improving the signal-to-noise ratio and improving the accuracy of electronic signal measurement, which may lead to improvements in a DNA sequencing scenario.

Referring to FIG. 1A, an initial lithography patterning step of a tunneling electrode channel is shown. A substrate 12 of the DNA sequencing device 10 has a first resist layer 14 formed thereon. An electrode channel or trench 16 is formed through the first resist layer 14 and substrate 12. The electrode channel 16 may pass completely through the first resist layer 14. The electrode channel 16 may pass through only a portion of a thickness of the substrate 12, whereas in other embodiments the electrode channel 16 may pass completely through the substrate 12 as well. The substrate 12 may comprise a conductive or nonconductive material. A nonconductive or insulator layer may comprise silicone oxide ($SiO_2$). The resist layer (also referred to as a photoresist layers) may comprise, for example, ZEP material. The electrode channel 16 may be formed using, for example, etching.

The electrode channel 16 may have a width $W_1$ typically in the range of about 10 nm to about 20 nm. The height of the electrode channel 16 formed within the substrate 12 typically in the range of about 10 nm to about 20 nm. The electrode channel 16 patterning may be conducted using various lithography tools, such as, for example, deep ultraviolet (DUV) lithography, 193 nm lithography, e-beam lithography, nano-imprint lithography (NIL), or the like. The etching of the substrate may be conducted using, for example, reactive ion etching (RIE).

Figure 1B:
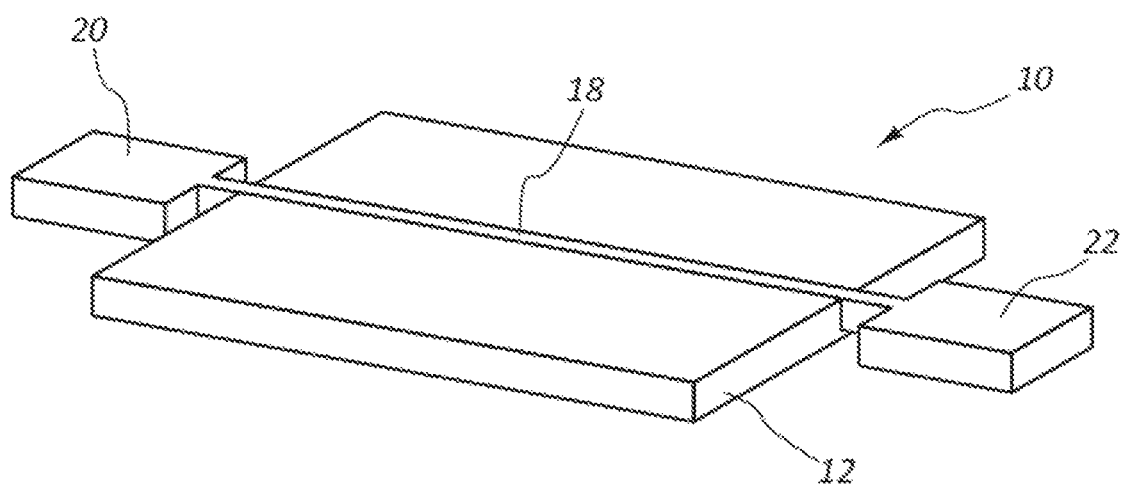

FIG. 1B illustrates another fabrication step in which the first resist later 14 has been removed and the electrode channel 16 has been filled with a conductive material to form an electrode 18. The electrode 18 has contacts 20, 22 formed at opposing ends thereof. In some embodiments, the electrode channel 16 shown in FIG. 1A is filled with the conductive material to form electrode 18 in an initial lift-off process, followed by stripping the resist material and excess portions of the electrode 18 positioned above the top surface of the substrate 12. In one example, the electrode 18 comprises chromium ($C_R$).

Figure 1C:
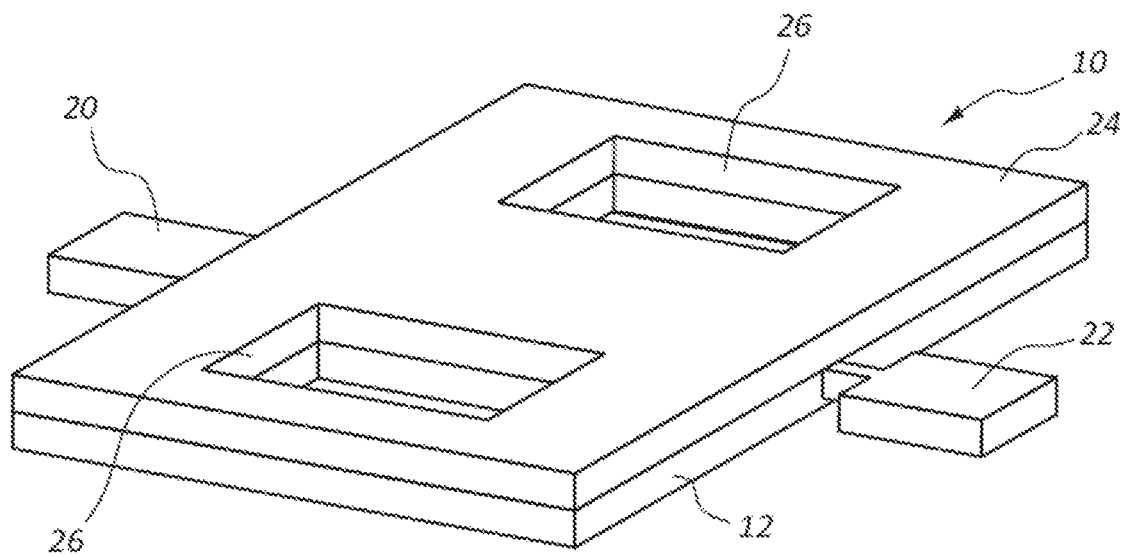

FIG. 1C illustrates the DNA sequencing device 10 at another fabrication stage in which a second resist layer 24 is formed on the substrate 12. A pair of contact pad apertures 26 are formed through the second resist layer 24 and into the substrate 12. The contact pad apertures 26 may be formed using, for example, an etching lithography step.

Figure 1D:
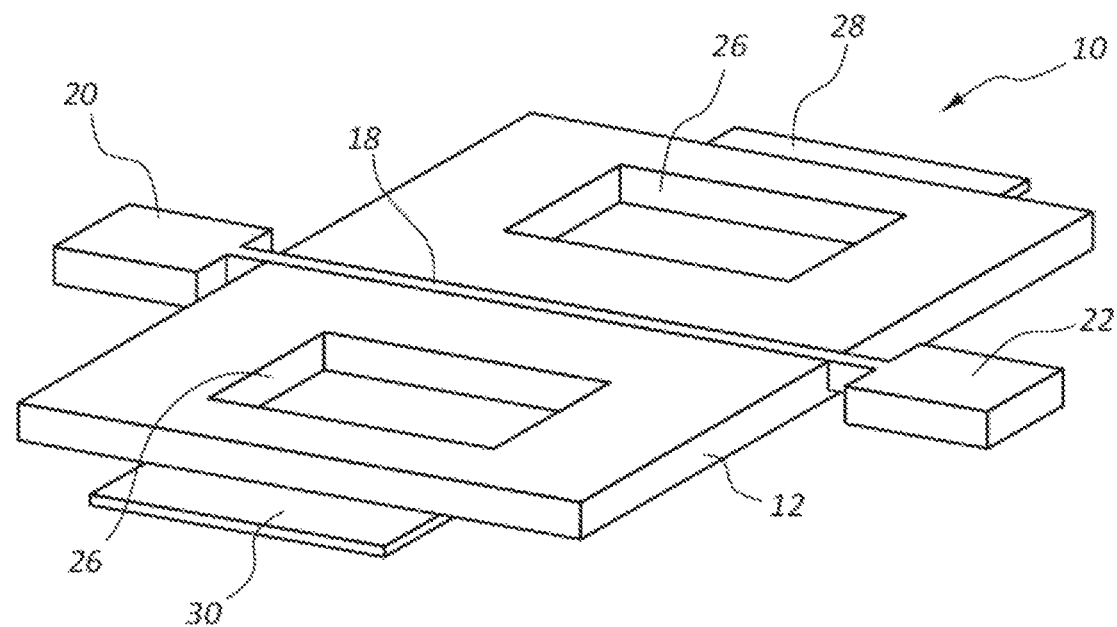

FIG. 1D illustrates a further fabrication step in which the second resist layer 24 is removed using, for example, a stripping process, and contact pads 28, 30 are formed beneath and/or within the contact pad apertures 26. The contact pads 28, 30 may comprise a conductive material such as Chromium (Cr). The contact pads 28, 30 may be formed using a lift-off process. Stripping the second resist layer 24 may be conducted prior to or after formation of the contact pads 28, 30.

Figure 1E:
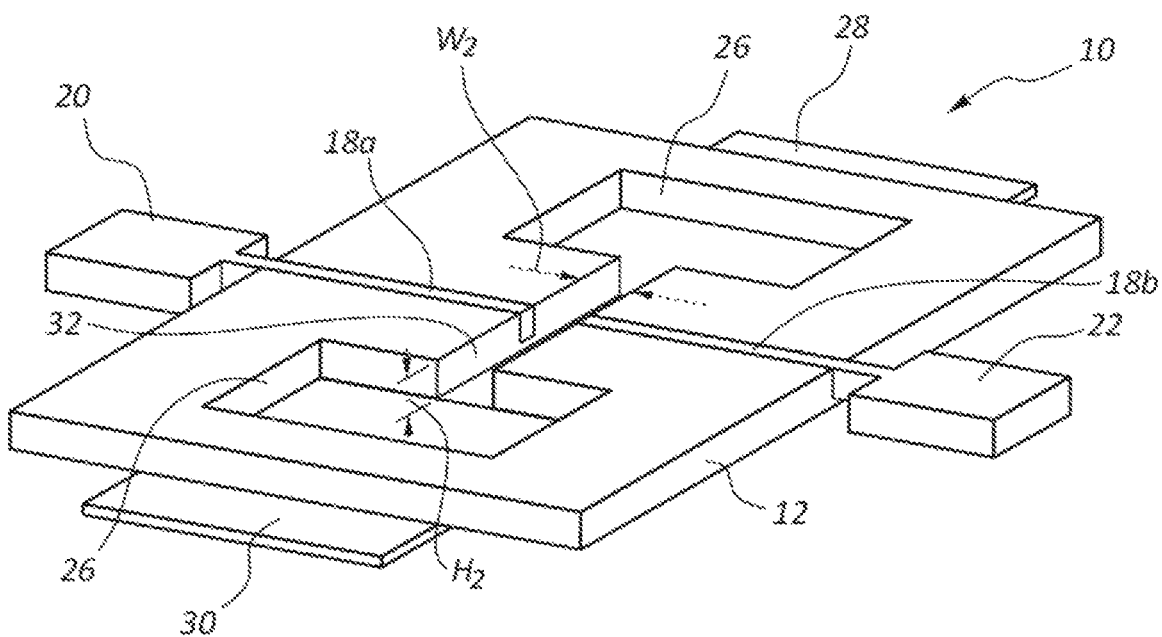

FIG. 1E illustrates a further fabrication step for DNA sequencing device 10 including patterning of a relatively narrow DNA channel 32. The channel 32 extends between the contact pads 28, 30. The channel 32 may have a width $W_2$ in the range of about 5 nm to about 10 nm. The channel 32 may have a height $H_2$ in the range of about 10 nm to about 20 nm. The channel 32 may extend through the electrode 18 thereby creating first and second electrode members 18a, 18b, which are electrically coupled to electrode contacts 20, 22, respectively. The electrode members 18a, 18b may be spaced apart by a gap $G_1$. The gap $G_1$ may be equal to the width $W_2$ of the channel 32.

Figure 1F:
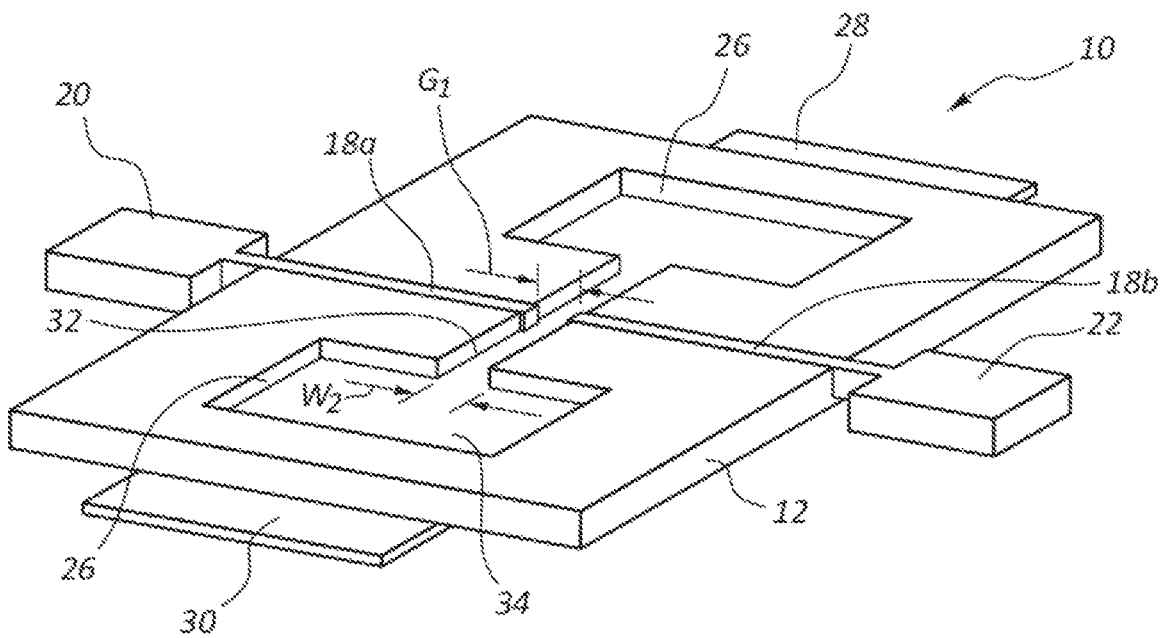

FIG. 1F illustrates deposition of a relatively thin insulator material 34 along the bottom of the contact pad apertures 26 (e.g., on a top surface of the contact pads 28, 30) and along the bottom of the DNA channel 32. The insulator material may comprise, for example, $SiO_2$.

Figure 1G:
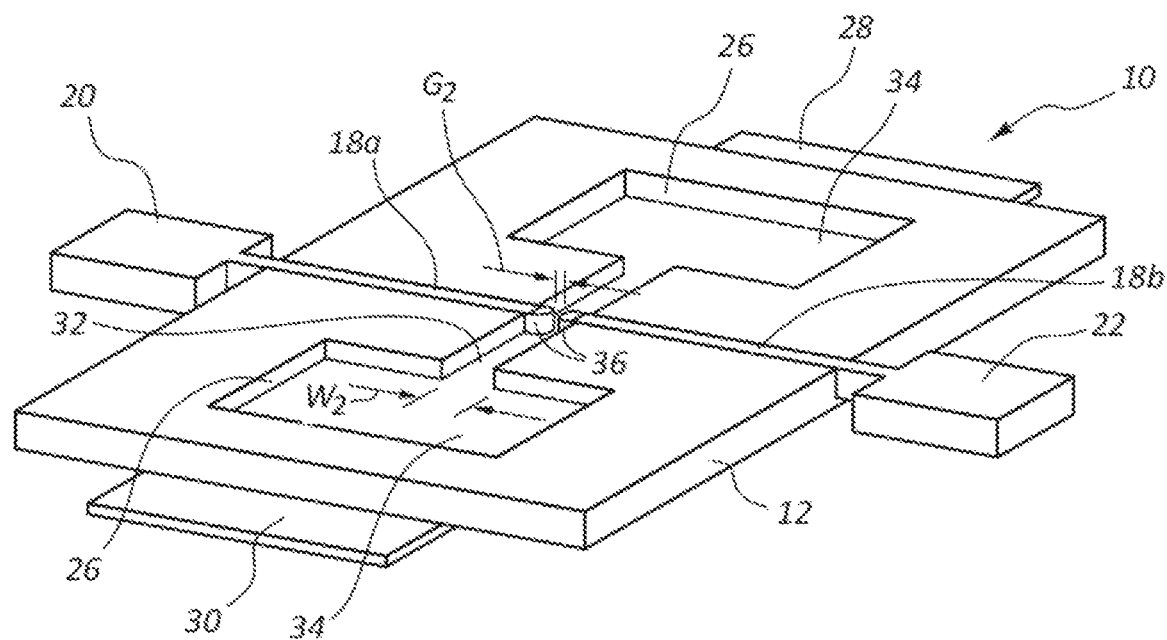

FIG. 1G illustrates a further fabrication step for the DNA sequencing device 10 in which the gap G between electrode members 18a, 18b is reduced using, for example, a plating process. The resulting gap $G_2$ between the electrode members 18a, 18b as a result of the plating process is preferably in the range of about 0.3 nm to about 2 nm (e.g., in the range of about 1 nm). The plating process may include, for example, electrode plating which, over time, gradually decreases the size of the gap G from the initial gap size $G_1$ to a reduced gap size $G_2$. An electrode plating process may provide accumulation of conductive material on the portion of the electrode members 18a, 18b which is exposed within the channel 32. Typically, the plating rate is closely controlled to achieve a desired size within the desired range discussed above.

FIG. 1G shows a shape for the plated tips 36 of the electrode members 18a, 18b that are somewhat rounded or contoured, and may have a reduced cross-sectional area. This contoured shape may reduce the cross-sectional area of the surfaces of the electrode members 18a, 18b facing each other across the gap $G_2$. This reduced surface area may lead to reduced noise in a measured electronic signal as a DNA strand passes through the gap G. The reduced noise may provide an increased signal-to-noise ratio, which may result in improved accuracy in determining a change in the electronic signal, which may enhance accuracy of distinguishing between different types of nucleotides of the DNA strand.

Figure 1H:
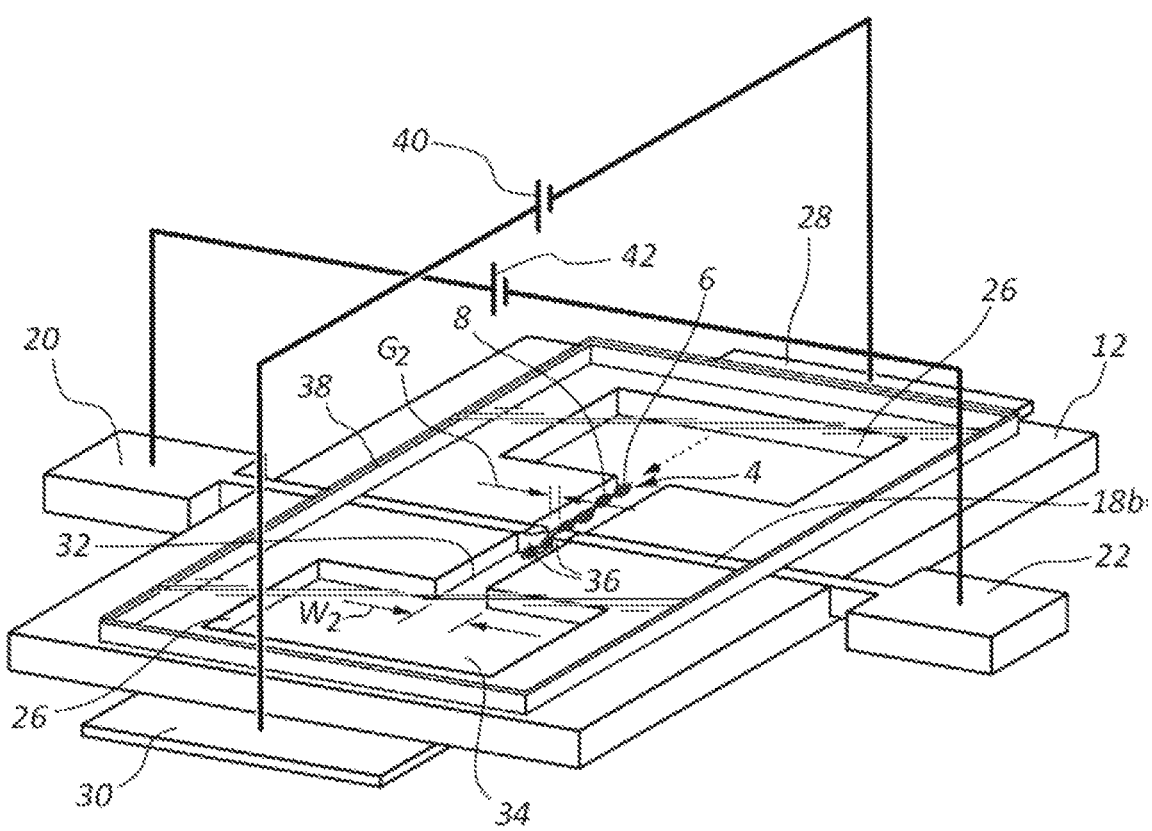

FIG. 1H illustrates a top sealing layer 38 formed on the substrate 12 to seal around at last portion of a perimeter of the channel 32 and/or contact pad apertures 26. The sealing layer 38 may comprise, for example, polydimethylsiloxane (PDMS). FIG. 1H also illustrates a partial DNA strand 4 having a backbone 8 to which a plurality of nucleotides 6 are mounted. The nucleotides (A,T,C,G), which may be referred to as bases, each have a unique electronic signal associated therewith as the DNA strand 4 passes through the gap G between the electrode members 18a, 18b. The electrode contacts 20, 22 may be connected to a controller or preamp 40 that detect the change in electronic signal as the DNA strand 4 passes through the gap G. An energy source 42 may create an electronic force that draws the DNA strand 4 into the channel 32 and through the gap G using, for example, electrophoresis.

The plating process used to reduce the size of gap G may enhance accuracy of detecting a change in electronic signal for each nucleotide of the DNA strand 4 passing through the gap G. An example method in accordance with the present disclosure may include formation of a nanoelectrode for use in a nanochannel or nanopore DNA sequencing device, wherein the nanoelectrode is formed at least in part using a plating process to control a gap size between electrode members of the nanoelectrode. The gap may be exposed within the nanochannel or nanopore. Further steps of the method may include drawing a DNA strand through the nanochannel and between the nanoelectrode members as part of determining a sequence of the nucleotides of the DNA strand.

Figure 2A:
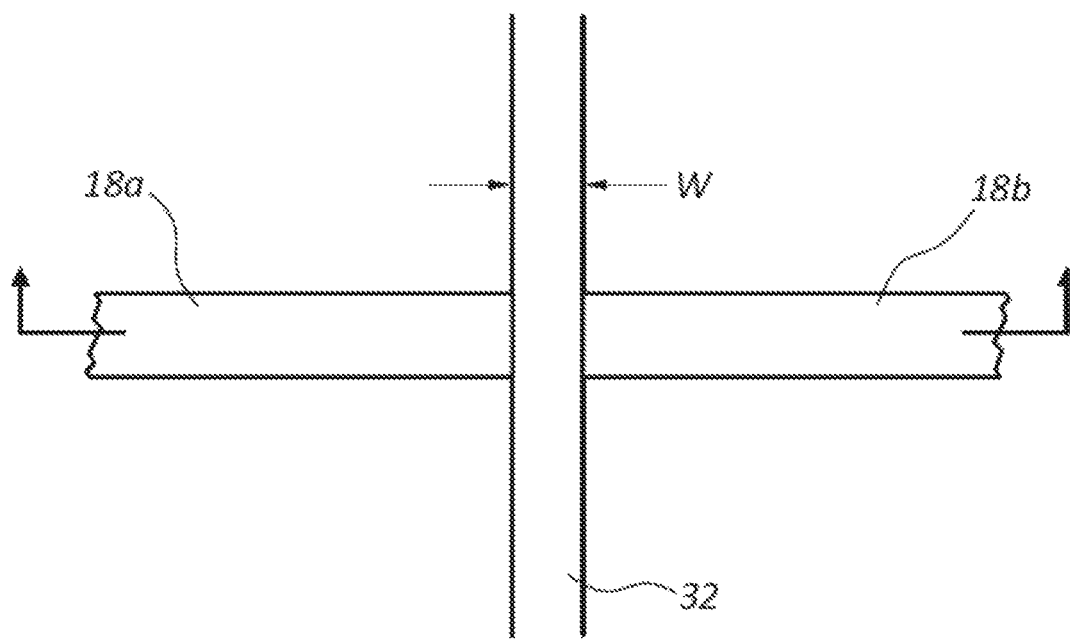
FIGS. 2A and 2B show a nanofluidic channel and electrodes in accordance with the present disclosure.
Figure 2B:
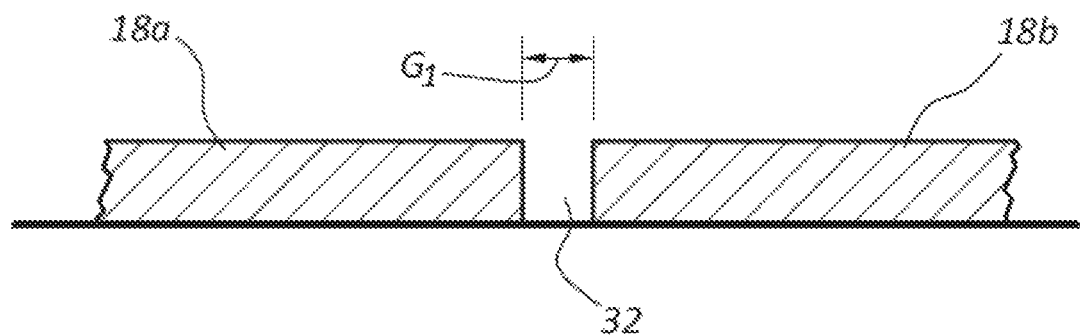
Figure 3A:
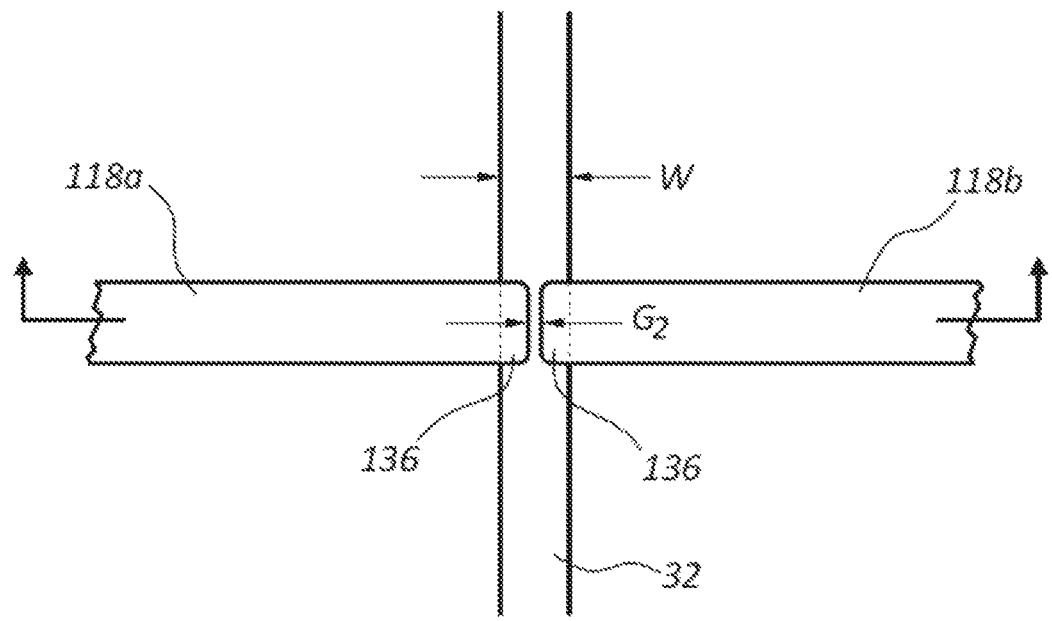
FIGS. 3A and 3B show a nanofluidic channel and electrodes in accordance with the present disclosure.
Figure 3B:
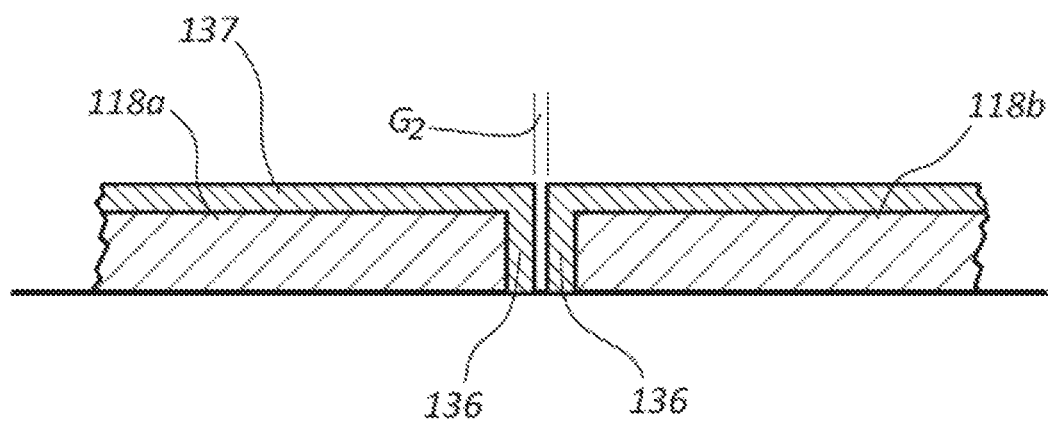

FIGS. 2A and 2B illustrate portions of a DNA sequencing device varying, for example, an intermediate fabrication process or step. A DNA sequencing device may include first and second electrode members 18a, 18b exposed within a nanofluidic channel 32 having a width W. The electrode members 18a, 18b are separated by an initial gap or spacing $G_1$. In accordance with the principles of the present disclosure, a plating process or other additive process may be used to reduce the spacing or gap between the electrode members to a gap size $G_2$, as shown in FIGS. 3A and 3B. The plating process may apply a conductive film or layer 137 on portions of the electrode members to create modified first and second electrode members 118a, 118b. The conductive film 137 may create plated tips 136 within the nanochannel 32, which results in a reduced size gap $G_2$. The gap $G_2$ is smaller than the gap G1 and the width W of the channel 32. Typically, the gap $G_2$ is on the order of about one 1 nanometer, and may be in the range of about 0.3 nm to about 2 nm.

Figure 4A:
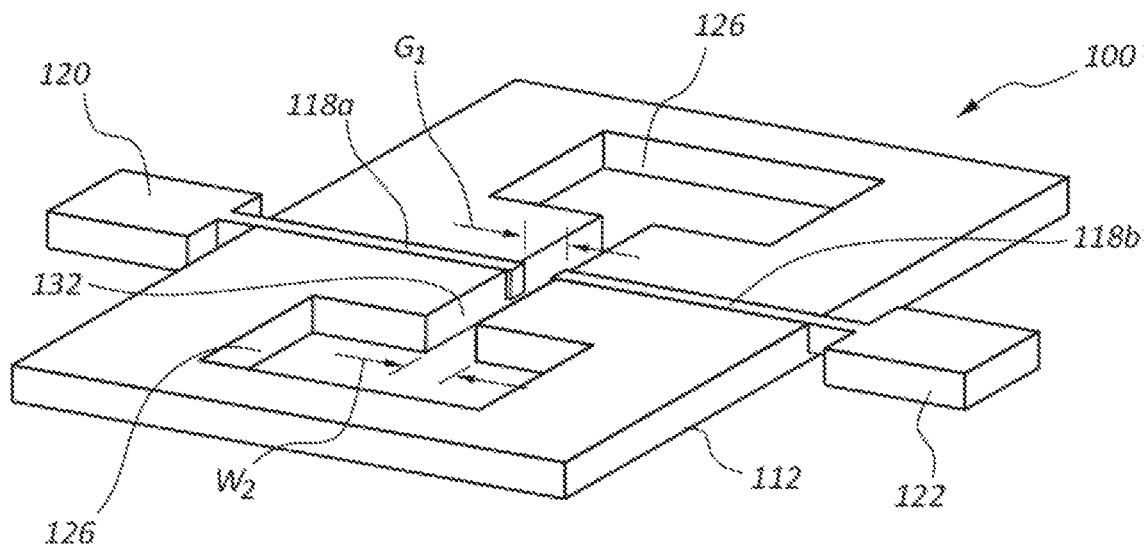
FIGS. 4A and 4B show a patterned nanofluidic channel and electrodes in different stages of fabrication in accordance with the present disclosure.
Figure 4B:
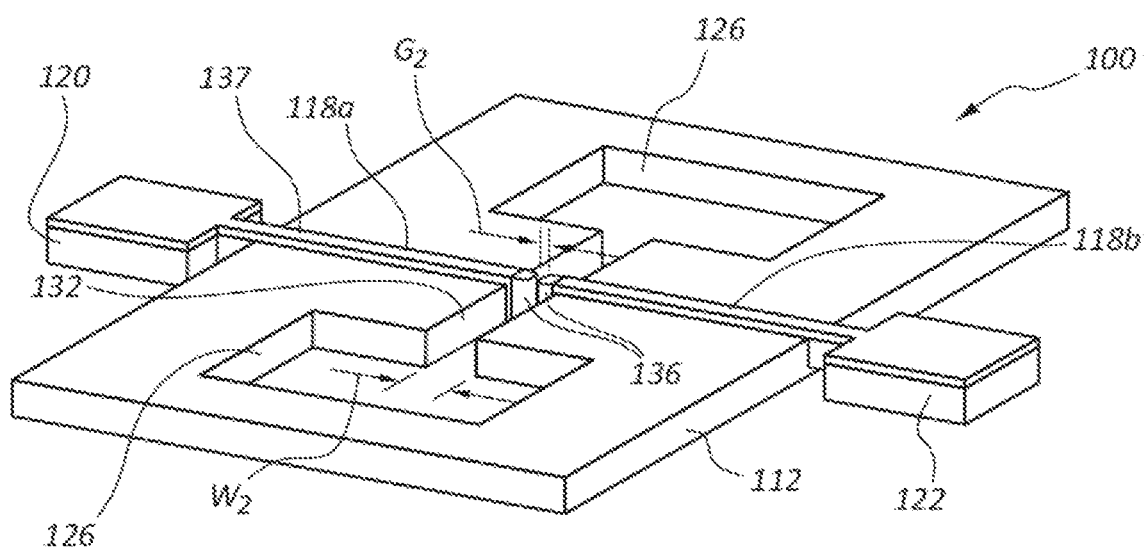

FIGS. 4A and 4B illustrate a DNA sequencing device 100 that includes the modified electrode members 118a, 118b as shown in FIG. 4B after application of a conductive film 137 and formation of plated tips 136. The DNA sequencing device 100 may include electrode contacts 120, 122 associated with the electrode members 118a, 118b, contact pad apertures 126, a DNA channel 132, and tips 136 positioned on the portions of electrode members 118a, 118b that are exposed within the channel 132. The tips 136 may be formed using a plating or other additive process. The tips 136 may have any desired shape and size. In at least one example, the tips 136 have a generally contoured shape that reduces in cross-sectional size getting closer to the gap $G_2$. The tips 136 of a given nanoelectrode may have different sizes and/or shapes.

Figure 5A:
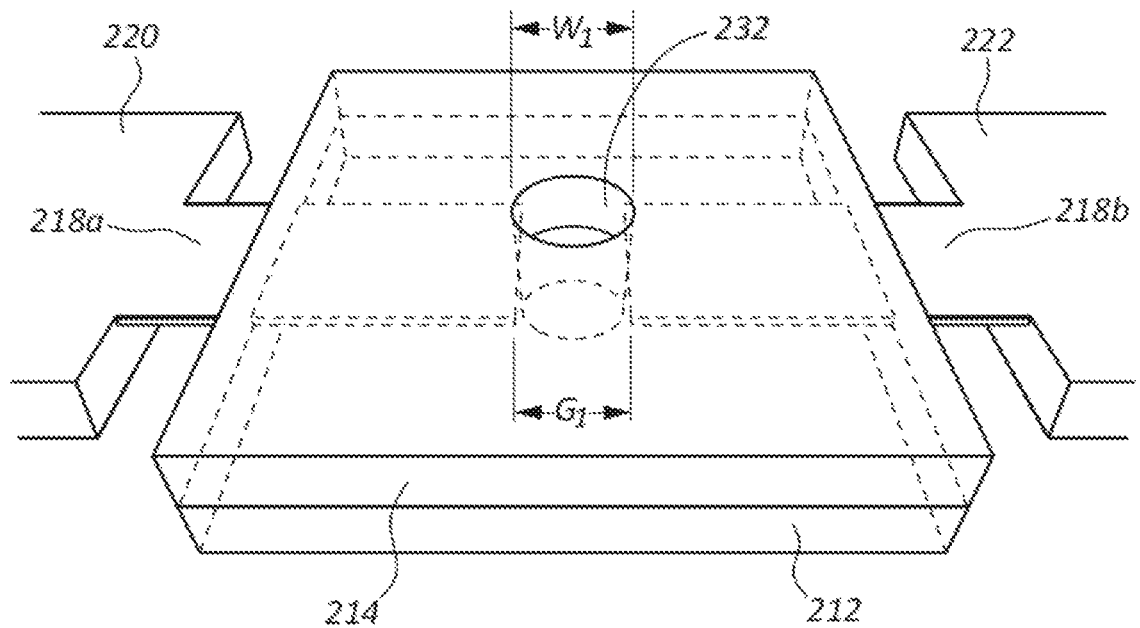
FIGS. 5A and 5B show different stages of fabricating a DNA nanofluidics channel in accordance with the present disclosure.
Figure 5B:
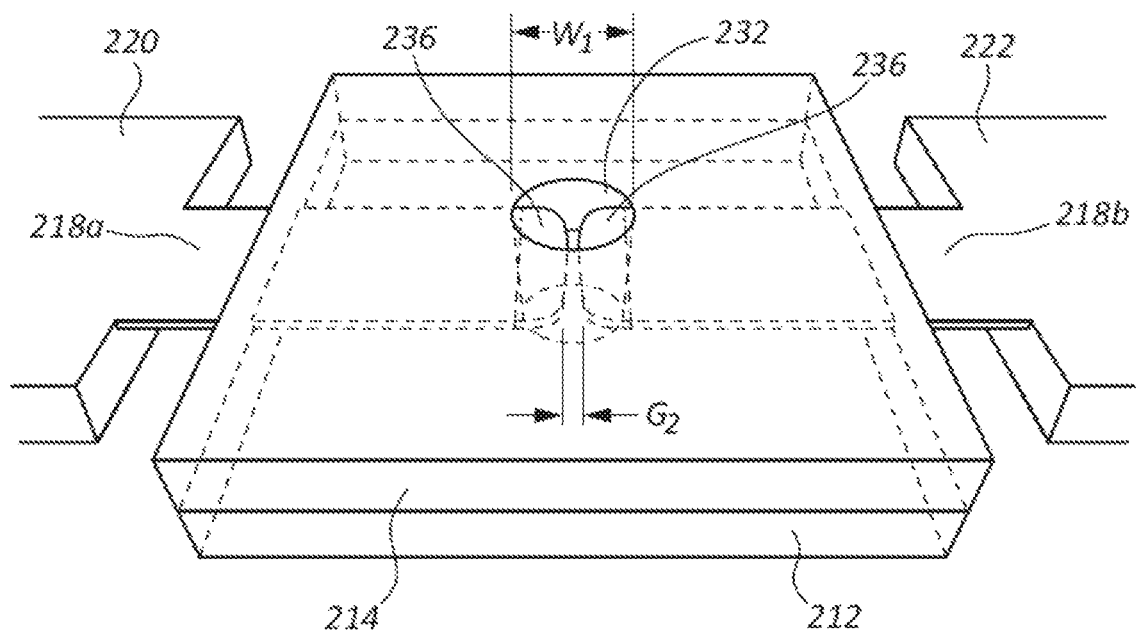

FIGS. 5A and 5B illustrate portions of a nanopore DNA sequencing device 200. FIG. 5A illustrates the device 200 comprising a substrate 212, an upper layer 214, first and second electrode members 218a, 218b exposed within a nanopore 232 passing through the substrate 212 and upper layer 214, and electrode contacts 220, 222 associated with the electrode members 218a, 218b. The electrode members 218a, 218b are spaced apart a distance $G_1$. FIG. 5B shows tips 236 formed on the electrode members 218a, 218b within the nanopore 232 to create a reduced sized gap $G_2$. The tips 236 may be formed using a plating or other additive process that reduced the spacing between the ends of the electrode members 218a, 218b from gap $G_1$ to gap $G_2$. The tips 236 may have any desired shape and size. The device 200 may be configured to pass a DNA strand vertically through the nanopore 232 and gap $G_2$, and determine a change in electronic signal as different nucleotides of the DNA strand pass through the gap $G_2$.

The plating fabrication steps disclosed herein may include isolating the electrode members and contact pads to the plating material (e.g., along the top surface of the substrate and/or within the channel/nanopore). The portions of DNA sequencing device that are not intended to be plated may be masked or covered in some way prior to initiating the plating process. The plating process may utilize a conductive material such as, for example, silver, gold, chromium, rhodium, zinc, zinc-nickel, tin, cadmium, and nickel.

Generally, the methods for fabricating tunneling electrodes disclosed herein provide spacing between electrode members by a gap on the order of about 1 nm or less. The methods disclosed herein may include forming an initial tunneling electrode configuration having an initial separation between the electrode member (e.g., using conventional lithography). A minimum separation between the electrode members may be limited by resolution limits of convectional lithography to about 10 nm or more. The methods disclosed herein may also include reducing a spacing or gap between the ends of the electrode members using, for example, a plating process such that the conductive plating material is added to surfaces of the existing electrode members over time. Alternatively, a selective atomic layer deposition (ALD) process may be used, such that a conductive material is deposited selectively and conformally onto the electrode surfaces. Plating and ALD processes may afford addition of conductive material in single atomic layer and/or molecular addition precision, thereby providing controlled closing of the gap to a size on the order of about 1 nm.

Figure 6:
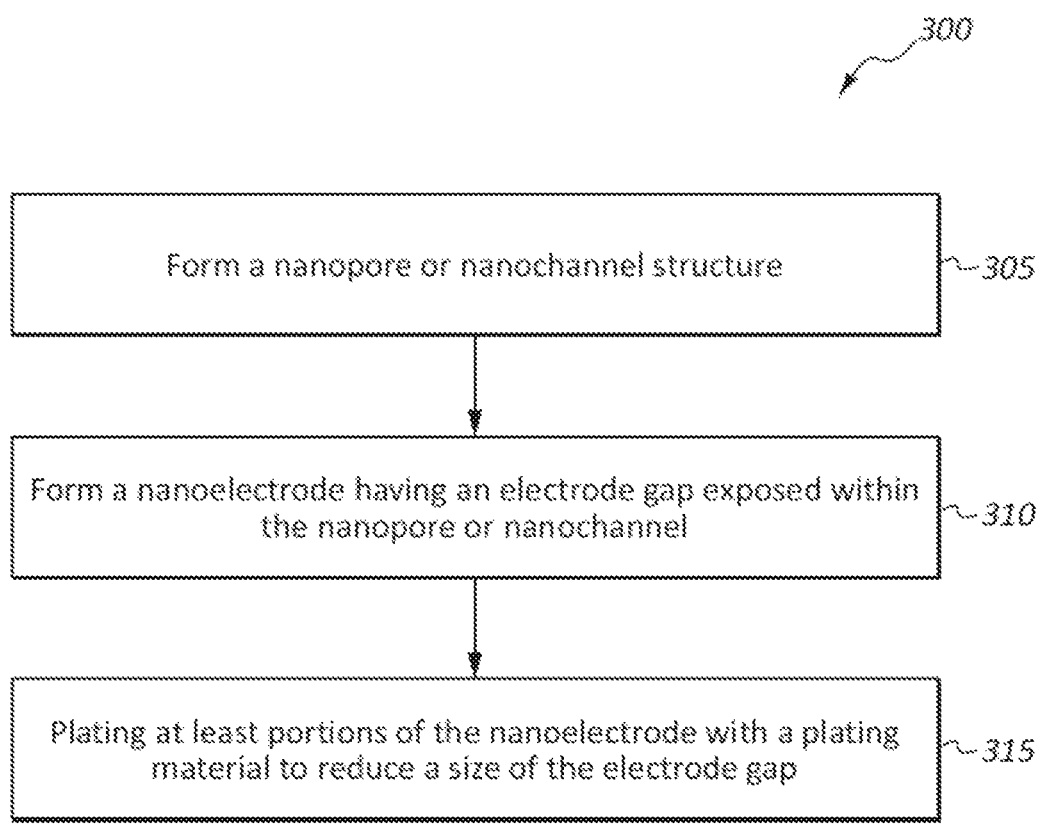
FIG. 6 is a flow chart illustrating an example of a method in accordance with various aspects of this disclosure.

FIG. 6 is a flow chart illustrating an example of a method 300 for fabrication of a DNA sequencing device, in accordance with various aspects of the present disclosure. One or more aspects of the method 300 may be implemented in conjunction with the devices 10, 100, 200 of FIGS. 1-5. In some examples, a computing device may execute one or more sets of codes to control functional elements of the DNA sequencing devices disclosed herein to perform one or more of the functions described below. Additionally, or alternatively, computing device, and/or storage device may perform one or more of the functions described below using special-purpose hardware.

At block 305, method 300 may include forming a nanopore or nanochannel structure. At block 310, the method includes forming a nanoelectrode having an electrode gap exposed within a nanopore or nanochannel. Block 315 includes plating or otherwise adding additional material to at least portions of the nanoelectrode with an additive (e.g., plating) material to reduce a size of the electrode gap.

The method 300 may also include reducing the size of the electrode gap to the range of about 0.3 nm to about 2 nm. The nanochannel and plating material may comprise a metallic material. The portions of the nanoelectrode that are plated may include end surfaces of the nanoelectrode that are exposed within the nanopore or nanochannel. The portions of the nanoelectrode that are plated may include top surfaces of the nanoelectrode that are arranged perpendicular to the end surfaces. The method 300 may further include lithography patterning a tunneling electrode channel in a resistor layer and insulator substrate, and forming the nanoelectrode may include forming a tunneling electrode in the channel. The method 300 may include forming a part of contact pad openings for DNA channeling by lithography and/or etching into the insulator substrate, filling the contact pad opening with contact pad material, forming the nanopore or nanochannel structure may include lithography patterning a DNA channel between the contact pads, depositing an insulating layer material over the contact pads and DNA channel, forming the nanopore or nanochannel structure with the electrode gap exposed within the nanopore or nanochannel, and/or depositing a sealing layer over the nanopore or nanochannel. The method 300 may include lithography patterning using at least of deep ultraviolet (DUV) lithography, 193 nm lithography, e-beam lithography, and nano-imprint lithography (NIL). The etching into the insulator substrate may include reactive ion etching (RIE). Forming the tunneling electrode in the channel may include a chromium (CR) lift-off process followed by stripping a resistor layer.

Figure 7:
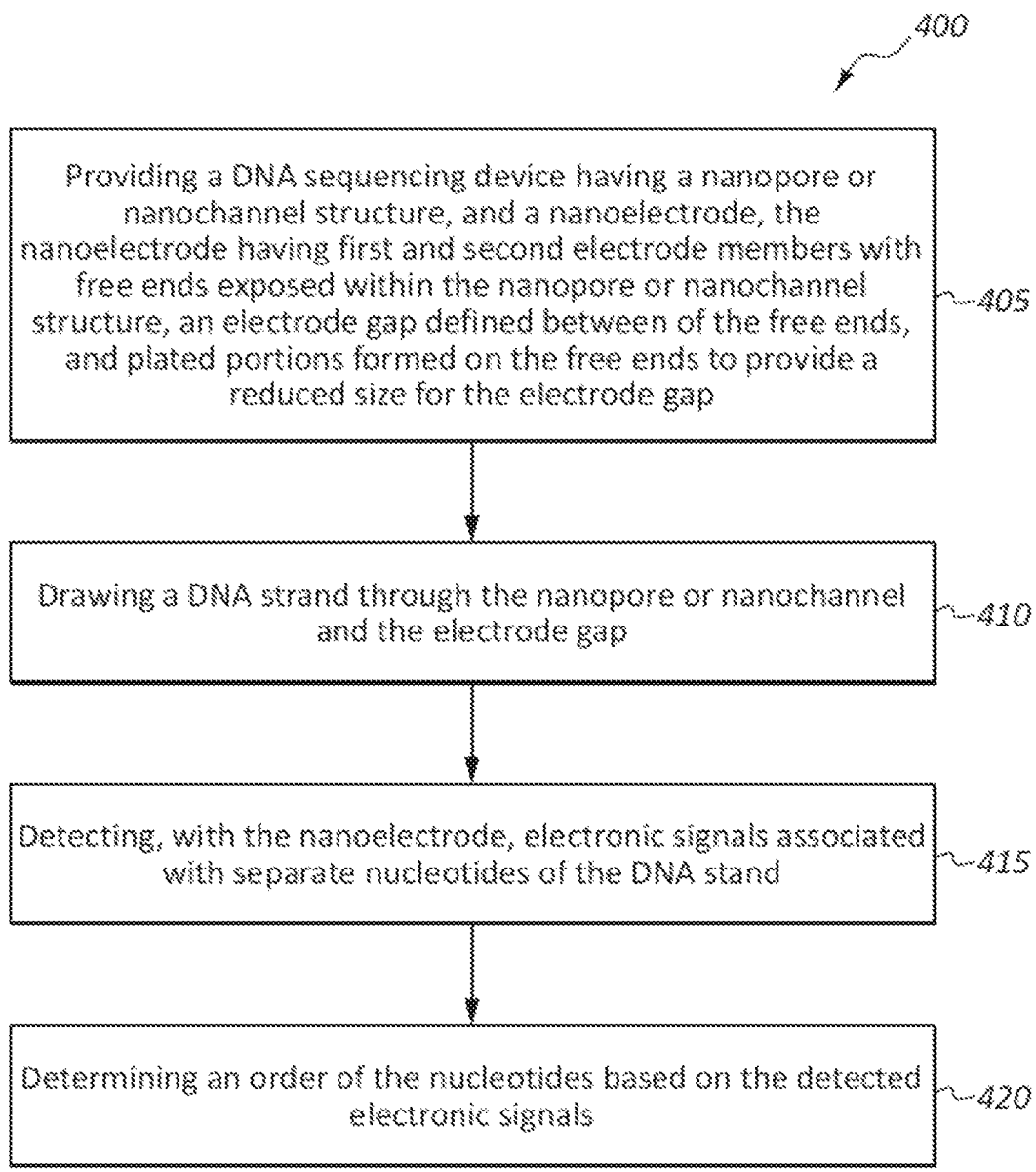
FIG. 7 is a flow chart illustrating an example of a method in accordance with various aspects of this disclosure.

FIG. 7 is a flow chart illustrating an example of a method 400 for DNA sequencing, in accordance with various aspects of the present disclosure. One or more aspects of the method 400 may be implemented in conjunction with the devices 10, 100, 200 of FIGS. 1-5B. In some examples, a computing device may execute one or more sets of codes to control functional elements of the DNA sequencing devices disclosed herein to perform one or more of the functions described below. Additionally, or alternatively, computing device, and/or storage device may perform one or more of the functions described below using special-purpose hardware.

The method 400 may include, at block 405, providing a DNA sequencing device having a nanopore or nanochannel structure, and a nanoelectrode. The nanoelectrode may have first and second electrode members with free ends exposed within the nanopore or nanochannel structure, an electrode gap defined between the free ends, and plated portions formed on the free ends to provide a reduced size for the electrode gap. Block 410 may include drawing a DNA strand through the nanopore or nanochannel and the electrode gap. Block 415 includes detecting, with the nanoelectrode, electronic signals associated with separate nucleotides of the DNA strand. Block 420 includes determining an order of the nucleotides based on the detected electronic signals.

The method 400 may further include reducing the size of the electrode gap with additional plating or other additive processes. The method 400 may include drawing the DNA strand through the nanopore or nanochannel and the electrode gap using electrophoresis processes.

The example methods 300, 400 may, in other embodiments, include fewer or additional steps that those illustrated in FIGS. 6 and 7. Further, many other methods and method steps may be possible based on the disclosures provided herein.

Figure 8:
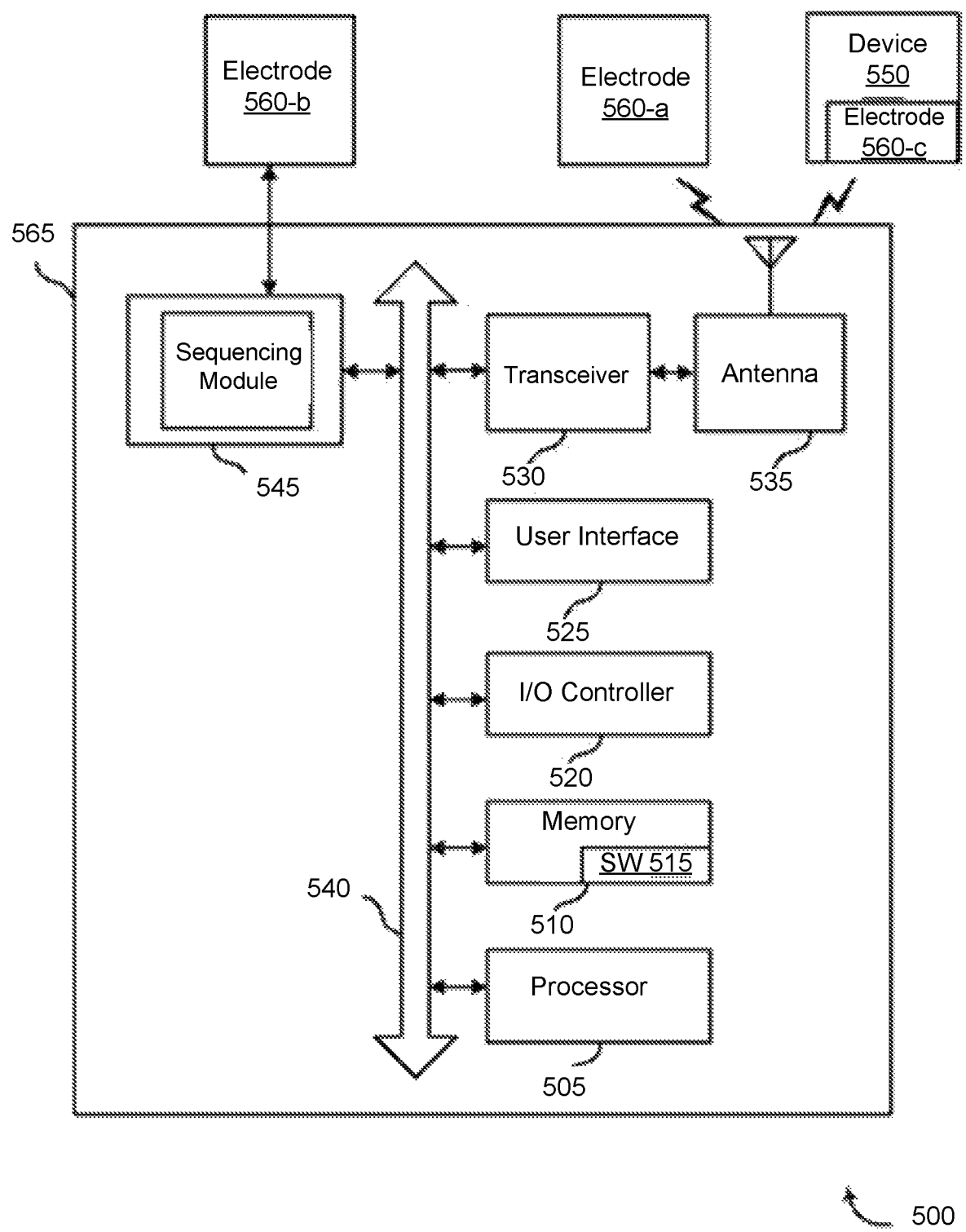
FIG. 8 shows a diagram of a system in accordance with various aspects of this disclosure.

FIG. 8 shows a system 500 for use with the DNA sequencing devices and systems shown in FIGS. 1-5. System 500 may include a control panel 565. Control panel 565 may be equivalent at least in part to a controller, control unit, processor or the like for use with the devices described above with reference to FIGS. 1-5. Control panel 565 may include sequencing module 545. The sequencing module 545 may provide communications with one or more electrodes 560 (also referred to as sensors or devices) directly or via other communication components, such as a transceiver 530 and/or antenna 535. The electrodes 560 may represent one or more of the electrodes 18, 118, 218, or pairs of such electrodes in any of the embodiments described above. The sequencing module 545 may perform or control various operations associated with, for example, the electrodes 18, 118, 218, actuators, controllers, or other components of the DNA sequencing devices and related systems as described above with reference to FIGS. 1-5.

Control panel 565 may also include a processor module 505, and memory 510 (including software/firmware code (SW) 515), an input/output controller module 520, a user interface module 525, a transceiver module 530, and one or more antennas 535 each of which may communicate, directly or indirectly, with one another (e.g., via one or more buses 540). The transceiver module 530 may communicate bi-directionally, via the one or more antennas 535, wired links, and/or wireless links, with one or more networks or remote devices. For example, the transceiver module 530 may communicate bi-directionally with one or more of device 550 and/or electrodes 560-a, 560-c. The device 550 may be components of the DNA sequencing devices and related systems and devices described with reference to FIGS. 1-3, or other devices in communication with such systems and devices. The transceiver 530 may include a modem to modulate the packets and provide the modulated packets to the one or more antennas 535 for transmission, and to demodulate packets received from the one or more antennas 535. In some embodiments (not shown) the transceiver may communicate bi-directionally with one or more of device 550, a remote control device, and/or electrodes 560-a, 560-c through a hardwired connection without necessarily using antenna 535. While a control panel or a control device (e.g., 565) may include a single antenna 535, the control panel or the control device may also have multiple antennas 535 capable of concurrently transmitting or receiving multiple wired and/or wireless transmissions. In some embodiments, one element of control panel 565 (e.g., one or more antennas 535, transceiver module 530, etc.) may provide a connection using wireless techniques, including digital cellular telephone connection, Cellular Digital Packet Data (CDPD) connection, digital satellite data connection, and/or another connection The signals associated with system 500 may include wireless communication signals such as radio frequency, electromagnetics, local area network (LAN), wide area network (WAN), virtual private network (VPN), wireless network (using 302.11, for example), 345 MHz, Z-WAVE®, cellular network (using 3G and/or LTE, for example), and/or other signals. The one or more antennas 535 and/or transceiver module 530 may include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 535 may receive signals or information specific and/or exclusive to itself. In other embodiments, each antenna 535 may receive signals or information not specific or exclusive to itself.

In some embodiments, one or more electrodes 560 (e.g., voltage, inductance, resistance, current, force, temperature, etc.) or devices 550 may connect to some element of system 500 via a network using one or more wired and/or wireless connections. In some embodiments, the user interface module 525 may include an audio device, such as an external speaker system, an external display device such as a display screen, and/or an input device (e.g., remote control device interfaced with the user interface module 525 directly and/or through I/O controller module 520).

One or more buses 540 may allow data communication between one or more elements of control panel 565 (e.g., processor module 505, memory 510, I/O controller module 520, user interface module 525, etc.).

The memory 510 may include random access memory (RAM), read only memory (ROM), flash RAM, and/or other types. The memory 510 may store computer-readable, computer-executable software/firmware code 515 including instructions that, when executed, cause the processor module 505 to perform various functions described in this disclosure (e.g., initiating an adjustment of a lighting system, etc.). Alternatively, the software/firmware code 515 may not be directly executable by the processor module 505 but may cause a computer (e.g., when compiled and executed) to perform functions described herein. Alternatively, the computer-readable, computer-executable software/firmware code 515 may not be directly executable by the processor module 505 but may be configured to cause a computer (e.g., when compiled and executed) to perform functions described herein. The processor module 505 may include an intelligent hardware device, e.g., a central processing unit (CPU), a microcontroller, an application-specific integrated circuit (ASIC), etc.

In some embodiments, the memory 510 can contain, among other things, the Basic Input-Output system (BIOS) which may control basic hardware and/or software operation such as the interaction with peripheral components or devices. For example, the sequencing module 545, and other modules and operational components of the control panel 565 used to implement the present systems and methods may be stored within the system memory 510. Applications resident with system 500 are generally stored on and accessed via a non-transitory computer readable medium, such as a hard disk drive or other storage medium. Additionally, applications can be in the form of electronic signals modulated in accordance with the application and data communication technology when accessed via a network interface (e.g., transceiver module 530, one or more antennas 535, etc.).

Many other devices and/or subsystems may be connected to one or may be included as one or more elements of system 500. In some embodiments, all of the elements shown in FIG. 8 need not be present to practice the present systems and methods. The devices and subsystems can be interconnected in different ways from that shown in FIG. 8. In some embodiments, an aspect of some operation of a system, such as that shown in FIG. 8, may be readily known in the art and are not discussed in detail in this application. Code to implement the present disclosure can be stored in a non-transitory computer-readable medium such as one or more of system memory 510 or other memory. The operating system provided on I/O controller module 520 may be iOS®, ANDROID®, MS-DOS®, MS-WINDOWS®, OS/2®, UNIX®, LINUX®, or another known operating system.

The transceiver module 530 may include a modem configured to modulate the packets and provide the modulated packets to the antennas 535 for transmission and/or to demodulate packets received from the antennas 535. While the control panel or control device (e.g., 505) may include a single antenna 535, the control panel or control device (e.g., 505) may have multiple antennas 535 capable of concurrently transmitting and/or receiving multiple wireless transmissions.

In some embodiments, the DNA sequencing device and systems described herein may be used to collect electronic signals associated with the nucleotides of a DNA strand passing through the gap between electrode pairs, and the collected electronic signals are processed at a different location. The processing may include electronically comparing the collected electronic signals to ranges of electronic signals associated with specific nucleotide types which have been previously determined and stored. In other embodiments, the DNA sequencing device includes capability of processing the collected electronic signals, conducting such comparison evaluations, and even formulating an order or sequence for the nucleotides of the DNA strand being evaluated.

INCORPORATION BY REFERENCE

The entire content of each of the previously filed provisional patent applications listed below are incorporated by reference in their entireties into this document, as are the related non-provisional patent applications of the same title filed concurrently with the present application. If the same term is used in both this document and one or more of the incorporated documents, then it should be interpreted to have the broadest meaning imparted by any one or combination of these sources unless the term has been explicitly defined to have a different meaning in this document. If there is an inconsistency between any of the following documents and this document, then this document shall govern. The incorporated subject matter should not be used to limit or narrow the scope of the explicitly recited or depicted subject matter.

U.S. Prov. App. No. 62/453,270, titled "SINGLE-MOLECULE DNA SEQUENCING METHOD USING CONFINED NANO-FLUIDIC CHANNEL AND SUB-NANOMETER ELECTRODE GAP," filed on 1 Feb. 2017, and U.S. patent application Ser. No. 15/886,442, titled "SINGLE-MOLECULE DNA SEQUENCING METHOD USING CONFINED NANO-FLUIDIC CHANNEL AND SUB-NANOMETER ELECTRODE GAP," filed on 1 Feb. 2018.

U.S. Prov. App. No. 62/453,398, titled "NANOFLUIDIC CHANNEL OPENING SIZE CONTROL USING ACTUATION," filed on 1 Feb. 2017, and U.S. patent application Ser. No. 15/886,483, titled "NANOFLUIDIC CHANNEL OPENING SIZE CONTROL USING ACTUATION," filed on 1 Feb. 2018.

U.S. Prov. App. No. 62/453,298, titled "FABRICATION OF NANOCHANNEL WITH INTEGRATED ELECTRODES FOR DNA SEQUENCING USING TUNNELING CURRENT," filed on 1 Feb. 2017, and U.S. patent application Ser. No. 15/886,511, titled "FABRICATION OF NANOCHANNEL WITH INTEGRATED ELECTRODES FOR DNA SEQUENCING USING TUNNELING CURRENT," filed on 1 Feb. 2018.

U.S. Prov. App. No. 62/453,307, titled "METHOD TO FABRICATE A NANOCHANNEL FOR DNA SEQUENCING BASED ON NARROW TRENCH PATTERNING PROCESS," filed on 1 Feb. 2017, and U.S. patent application Ser. No. 15/886,533, titled "METHOD TO FABRICATE A NANOCHANNEL FOR DNA SEQUENCING BASED ON NARROW TRENCH PATTERNING PROCESS," filed on 1 Feb. 2018.

U.S. Prov. App. No. 62/453,323, titled "FABRICATION OF A DEVICE FOR SINGLE-MOLECULE DNA SEQUENCING USING SIDEWALL LITHOGRAPHY," filed on 1 Feb. 2017, and U.S. patent application Ser. No. 15/886,560, titled "FABRICATION OF A DEVICE FOR SINGLE-MOLECULE DNA SEQUENCING USING SIDEWALL LITHOGRAPHY," filed on 1 Feb. 2018.

U.S. Prov. App. No. 62/453,346, titled "NANOSTRUCTURES TO CONTROL DNA STRAND ORIENTATION AND POSITION LOCATION FOR TRANSVERSE DNA SEQUENCING," filed on 1 Feb. 2017, and U.S. patent application Ser. No. 15/886,608, titled "NANOSTRUCTURES TO CONTROL DNA STRAND ORIENTATION AND POSITION LOCATION FOR TRANSVERSE DNA SEQUENCING," filed on 1 Feb. 2018.

U.S. Prov. App. No. 62/453,365, titled "FABRICATION OF WEDGE SHAPED ELECTRODE FOR ENHANCED DNA SEQUENCING USING TUNNELING CURRENT," filed on 1 Feb. 2017, and U.S. patent application Ser. No. 15/886,661, titled "FABRICATION OF WEDGE SHAPED ELECTRODE FOR ENHANCED DNA SEQUENCING USING TUNNELING CURRENT," filed on 1 Feb. 2018.

U.S. Prov. App. No. 62/453,329, titled "DIRECT SEQUENCING DEVICE WITH A TOM-BOTTOM ELECTRODE PAIR," filed on 1 Feb. 2017, and U.S. patent application Ser. No. 15/886,685, titled "DIRECT SEQUENCING DEVICE WITH A TOM-BOTTOM ELECTRODE PAIR," filed on 1 Feb. 2018.

U.S. Prov. App. No. 62/453,376, titled "MICRO AND NANOFLUIDIC CHANNEL CONTROLLED ACTUATION TO OPEN CHANNEL GAP," filed on 1 Feb. 2017.

U.S. Prov. App. No. 62/469,393, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2017, and U.S. patent application Ser. No. 15/886,736, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2018.

U.S. Prov. App. No. 62/469,409, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2017, and U.S. patent application Ser. No. 15/886,723, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2018.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC (i.e., A and B and C).

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A DNA sequencing device, comprising:
   a nanopore or nanochannel structure having a width in the range of about 5 nm to about 20 nm; and
   a nanoelectrode comprising:
      electrode members having free ends exposed within the nanopore or nanochannel structure, the free ends comprising plated portions defining an electrode gap in the range of about 0.3 nm to about 2.0 nm.

2. The DNA sequencing device of claim 1, wherein the nanopore or nanochannel structure is formed in an insulator substrate, the insulator substrate comprising $SiO_2$ or glass.

3. The DNA sequencing device of claim 1, wherein the nanopore or nanochannel structure has a width in the range of about 10 nm to about 20 nm.

4. The DNA sequencing device of claim 1, further comprising:
   electrode contacts electrically connected to the nanoelectrode; and a controller electrically connected to the electrode contacts and operable to detect an electronic signal measured between the electrode members.

5. The DNA sequencing device of claim 1, further comprising an energy source operable to draw a DNA strand through the nanopore or nanochannel.

6. A method of DNA sequencing, comprising:
providing a DNA sequencing device having a nanopore or nanochannel structure having a width of about 5 nm to about 20 nm, and a nanoelectrode, the nanoelectrode having first and second electrode members with free ends exposed within the nanopore or nanochannel structure, the free ends comprising plated portions, the plated portions defining an electrode gap of about 0.3 nm to about 2.0 nm;
drawing a DNA strand through the nanopore or nanochannel and the electrode gap;
detecting, with the nanoelectrode, electronic signals associated with separate nucleotides of the DNA strand;
determining an order of the nucleotides based on the detected electronic signals.

7. The method of claim 6, wherein the plated portions comprise a different material from the first and second electrode members.

8. The method of claim 6, wherein the DNA sequencing device further comprises a controller operable to conduct the determining of the order of the nucleotides.

9. The method of claim 6, wherein the width of the nanopore or nanochannel is in the range of about 10 nm to about 20 nm.

10. The method of claim 6, wherein a height of the nanopore or nanochannel is in the range of about 10 nm to about 20 nm.

11. The method of claim 6, wherein the nanopore or nanochannel structure is formed in an insulator substrate, the insulator substrate comprising $SiO_2$ or glass.

* * * * *